United States Patent [19]

Kurimoto et al.

[11] Patent Number: 5,151,542
[45] Date of Patent: Sep. 29, 1992

[54] PROCESS FOR PREPARING DI-TERT.-BUTYL DICARBONATE

[75] Inventors: Isao Kurimoto, Toyonaka; Masayoshi Minai, Moriyama, both of Japan

[73] Assignee: Sumitomo Chemical Co., Ltd., Osaka, Japan

[21] Appl. No.: 731,007

[22] Filed: Jul. 16, 1991

[30] Foreign Application Priority Data

Jul. 23, 1990 [JP] Japan .................................. 2-195412
Aug. 27, 1990 [JP] Japan .................................. 2-226225
Feb. 18, 1991 [JP] Japan .................................. 3-023491
Feb. 18, 1991 [JP] Japan .................................. 3-023494

[51] Int. Cl.$^5$ .............................................. C07C 69/96
[52] U.S. Cl. ...................................................... 558/277
[58] Field of Search ......................................... 558/277

[56] References Cited

FOREIGN PATENT DOCUMENTS 247845 12/1987 Czechoslovakia .
247846 12/1987 Czechoslovakia .
257157 2/1989 Czechoslovakia .
260076 5/1989 Czechoslovakia .
0256559 2/1988 European Pat. Off. ............ 558/277
195027 8/1986 Japan .
186847 7/1989 Japan .

OTHER PUBLICATIONS

Chemical Abstracts, vol. 109, No. 2, issued Jul. 11, 1988 (Columbus, Ohio, U.S.A.), Borovicka et al., "Manufacture of di-tertiary-butyl dicarbonane", Abs. No. 8418g.
Chemical Abstracts, vol. 109, No. 2, issued Jul. 11, 1988 (Columbus, Ohio, U.S.A.) Trojanek et al., "Process for the manufacture of di-tertiary-butyl dicarbonane", Abs. No. 8419h.
Chemical Abstracts, vol. 111, No. 11, issued Sep. 11, 1989 (Columbus, Ohio, U.S.A.) Trojanek et al., "Preparation of di-tert-butyl dicarbonate as a peptide reagent", Abs. No. 96670c.
Chemical Abstracts, vol. 111, No. 25, issued Dec. 18, 1989 (Columbus, Ohio, U.S.A.) Borovicka et al., "Preparation of di-tert-butyl dicarbonate", Abs. No. 232083t.
J. Org. Chem., vol. 43, No. 12, 1978.
Org. Synth., 57, 45 (1975).
Zh. Org. Khim. 15(1), 106-9, 1979.

Primary Examiner—Jose G. Dees
Assistant Examiner—Porfirio Nazario
Attorney, Agent, or Firm—Birch, Stewart, Kolasch & Birch

[57] ABSTRACT

Di-tert.-butyl dicarbonate having a high purity is prepared by reacting alkali metal tert.-butyl carbonate with methanesulfonyl chloride optionally in the presence of a phase transfer catalyst or an aromatic amine.

12 Claims, No Drawings

PROCESS FOR PREPARING DI-TERT.-BUTYL DICARBONATE

BACKGROUND OF THE INVENTION

1. Field of the Invention

The present invention relates to a novel process for preparing di-tert.-butyl dicarbonate (hereinafter referred to as "DIBOC"), which is useful as a protecting agent of an amino group.

2. Description of the Related Art

DIBOC is known as an amino group-protecting agent through tert.-butoxycarbonylation of various amino groups. The tert.-butoxycarbonylation has various advantages that its reactivity is good and post-treatment is simple since by-products are substantially tert.-butyl alcohol and carbon dioxide.

Preparation processes of DIBOC are roughly classified in three groups.

The first process is disclosed in Org. Synth., 57, 45 (1975) and comprises reacting potassium tert.-butoxide with carbon dioxide in tetrahydrofuran, reacting resulting potassium tert.-butyl carbonate with phosgene to obtain ditert.-butyl tricarbonate, isolating and purifying it, and then decarboxylating it in the presence of a tertiary amine such as 1,4-diazabicyclo[2.2.2]octane as a catalyst to obtain DIBOC. In connection with this process, an improved process in which di-tert.-butyl tricarbonate is not isolated or purified (cf. Japanese Patent Kokai Publication No. 51358/1988).

The second process is disclosed in Japanese Patent Kokai Publication No. 186847/1989 and proposes the use of thionyl chloride in place of phosgene in the first process.

The third process is disclosed in Zh. Org. Khim., 15 (1), 106 (1975) and comprises reacting sodium tert.-butoxide with carbon dioxide in an aromatic hydrocarbon such as toluene, reacting a part of resulting sodium tert.-butyl carbonate with benzoyl chloride which is substituted with at least one nitro group or trichloroacetyl chloride in a mixed solvent of an aromatic hydrocarbon (e.g. toluene) and N,N-dimethylformamide to generate an active mixed acid anhydride in a reaction system, and then reacting the mixed acid anhydride with an excess amount of sodium tert.-butyl carbonate to obtain DIBOC. In a similar process disclosed in CS (Czechoslovakian Patent) 247845 and CS 247846, benzenesulfonyl chloride or p-toluenesulfonyl chloride is used in place of the acyl chloride in the above process. Further improvement of this process is disclosed in CS 257157 and CS 260076.

In the industrial production of DIBOC, each process has its own defects. That is, in the first process, highly toxic phosgene should be used, and in the second process, a yield of DIBOC is low though the problem of phosgene is solved. In the third process, the earlier report was unsatisfactory since a long reaction time, for example, 15 to 20 hours was required, while the later improvement could shorten the reaction time.

Since DIBOC is thermally unstable (cf. J. Org. Chem, 43, 2410 (1978)), isolation of DIBOC from the reaction mixture should be done by distillation under high vacuum which is not easy in the industrial scale in any of the above processes. Then, further improvement of a process for preparing DIBOC has been sought.

SUMMARY OF THE INVENTION

An object of the present invention is to provide a process for preparing DIBOC which solves the above problems of the conventional processes.

According to the present invention, there is provided a process for preparing DIBOC which comprises reacting alkali metal tert.-butyl carbonate with methanesulfonyl chloride.

DETAILED DESCRIPTION OF THE INVENTION

As the alkali metal tert.-butyl carbonate, sodium tert.-butyl carbonate and potassium tert.-butyl carbonate are preferred.

The alkali metal tert.-butyl carbonate may be prepared by reacting a corresponding alkali metal tert.-butoxide with carbon dioxide. This reaction is carried out by blowing carbon dioxide through a solution or suspension of the alkali metal tert.-butoxide in an organic solvent at a temperature of from $-50°$ to $+70°$ C., preferably from $-40°$ to $\pm 40°$ C. Usually 0.5 to 10 moles, preferably 1 to 3 moles of carbon dioxide is used per one mole of the alkali metal tert.-butoxide.

Examples of the organic solvent used in this reaction are aromatic hydrocarbons (e.g. benzene, toluene, xylene, etc.), aliphatic hydrocarbons (e.g. pentane, hexane, heptane, octane, decane, cyclohexane, etc.), ethers (e.g. tetrahydrofuran, dioxane, diethyl ether, diisopropyl ether, dibutyl ether, etc.), or mixtures thereof. Practically, it is preferred to use the aromatic or aliphatic hydrocarbons or their mixture since they will give a good result in the subsequent reaction with methanesulfonyl chloride. In such case, the alkali metal tert.-butyl carbonate can be used without isolation in the subsequent reaction with methanesulfonyl chloride. When a solvent other than the aromatic or aliphatic hydrocarbons is used, the tert.-butyl alkali metal carbonate is preferably isolated and then reacted with methanesulfonyl chloride.

By the reaction of the resulting tert.-butyl alkali metal carbonate with methanesulfonyl chloride in a solvent, DIBOC is prepared. As the solvent used in this step, preferably a non-polar solvent such as an aromatic hydrocarbon (e.g. benzene, toluene, xylene, etc.), an aliphatic hydrocarbon (e.g. pentane, hexane, heptane, octane, decane, cyclohexane, etc.) or a mixture thereof is used. Among them, the aliphatic hydrocarbon is more preferred. An amount of the solvent is not critical.

If the process of the present invention is carried out in a mixed solvent comprising the aromatic or aliphatic hydrocarbon and an aprotic polar solvent (e.g. N,N-dimethylformamide) or an alcohol (e.g. tert.-butyl alcohol), the yield is unfavorably decreased.

An amount of methanesulfonyl chloride is usually from 0.4 to 0.6 mole, preferably from 0.45 to 0.55 mole per one mole of the alkali metal tert.-butyl carbonate. Outside this range, the yield of DIBOC tends to decrease.

A reaction temperature is usually from $-50°$ to $50°$ C., preferably from $-40°$ to $+40°$ C. When the reaction temperature is too low, a reaction rate becomes low, while when the reaction temperature is too high, the starting material, the intermediate mixed acid anhydride and/or the product are unpreferably decomposed.

A reaction time depends on the reaction temperature and cannot be fixed. Usually, it is from 0.5 to 10 hours.

In the present invention, the alkali metal tert.-butyl carbonate and methanesulfonyl chloride are reacted. When this reaction is carried out in the presence of a phase transfer catalyst or an aromatic amine, the yield of DIBOC is increased and the reaction time is shortened. In some cases, a combination of the phase transfer catalyst and the aromatic amine will further increase the yield. When sodium tert.-butyl carbonate is used as one of the starting materials, at least one of the phase transfer catalyst and the aromatic amine should be used.

The phase transfer catalyst includes quaternary ammonium salts and pyridinium salts. Specific examples of these compounds are as follows:

Quaternary ammonium salts

Tetramethylammonium fluoride, tetramethylammonium chloride, tetramethylammonium bromide, tetramethylammonium iodide, tetramethylammonium perchlorate, tetramethylammonium tetrafluoroborate, tetramethylammonium hexafluorophosphate, tetraethylammonium fluoride, tetraethylammonium chloride, tetraethylammonium bromide, tetraethylammonium iodide, tetraethylammonium perchlorate, tetraethylammonium tetrafluoroborate, tetraethylammonium acetate, tetraethylammonium p-toluenesulfonate, tetra-n-propylammonium chloride, tetran-propylammonium bromide, tetra-n-propylammonium iodide, tetra-n-propylammonium perchlorate, tetra-n-butylammonium fluoride, tetra-n-butylammonium chloride, tetra-n-butylammonium bromide, tetra-n-butylammonium iodide, tetra-n-butylammonium perchlorate, tetra-n-butylammonium hydrogensulfate, tetra-n-pentylammonium bromide, tetra-n-hexylammonium bromide, tetra-n-heptylammonium bromide, tetra-n-octylammonium bromide, phenyltrimethylammonium chloride, phenyltrimethylammonium bromide, phenyltrimethylammonium iodide, phenyltriethylammonium chloride, benzyltrimethylammonium chloride, benzyltrimethylammonium bromide, benzyltrimethylammonium iodide, benzyltriethylammonium chloride, benzyltriethylammonium bromide, benzyltri-n-butylammonium chloride, benzylcetyldimethylammonium chloride, benzyldimethylstearylammonium chloride, cetyltrimethylammonium chloride, cetyltrimethylammonium bromide, lauryltrimethylammonium chloride, lauryltrimethylammonium bromide, methyltri-n-octylammonium chloride, etc.

Pyridinium salts

N-n-butylpyridinium chloride, N-n-butylpyridinium bromide, N-n-pentylpyridinium chloride, N-n-pentylpyridinium bromide, N-n-octylpyridinium chloride, N-n-octylpyridinium bromide, N-cetylpyridinium chloride, N-cetylpyridinium bromide, N-laurylpyridinium chloride, N-n-laurylpyridinium bromide, N-n-butyl-2-picolinium chloride, N-n-butyl-2-picolinium bromide, N-n-pentyl-2-picolinium chloride, N-n-pentyl-2-picolinium bromide, N-n-octyl-2-picolinium chloride, N-n-octyl-2-picolinium bromide, N-cetyl-2-picolinium chloride, N-cetyl-2-picolinium bromide, N-lauryl-2-picolinium chloride, N-lauryl-2-picolinium bromide, N-n-butyl-3-picolinium chloride, N-n-butyl-3-picolinium bromide, N-n-pentyl-3-picolinium chloride, N-n-pentyl-3-picolinium bromide, N-n-octyl-3-picolinium chloride, N-n-octyl-3-picolinium bromide, N-cetyl-3-picolinium chloride, N-cetyl-3-picolinium bromide, N-lauryl-3-picolinium chloride, N-lauryl-3-picolinium bromide, N-n-butyl-4-picolinium chloride, N-n-butyl-4-picolinium bromide, N-n-pentyl-4-picolinium chloride, N-n-pentyl-4-picolinium bromide, N-n-octyl-4-picolinium chloride, N-n-octyl-4-picolinium bromide, N-cetyl-4-picolinium chloride, N-cetyl-4-picolinium bromide, N-lauryl-4-picolinium chloride, N-lauryl-4-picolinium bromide, etc.

In the process of the present invention, the quaternary ammonium salts and the pyridinium salts are used independently or as a mixture of two or more of them. Among them, the N-alkylpyridinium salts are more preferred.

An amount of the phase transfer catalyst is usually not more than 200% by mole, preferably from 0.1 to 100% by mole based on the amount of the starting alkali metal tert.-butyl carbonate.

Specific examples of the aromatic amine to be used in the process of the present invention are pyridine, 2-picoline, 3-picoline, 4-picoline, lutidine, collidine, etc. An amount of such amine is usually not more than 200% by mole, preferably from 0.1 to 100% by mole based on the amount of the alkali metal tert.-butyl carbonate.

DIBOC can be recovered from the reaction mixture by washing the reaction mixture with water and evaporating off the solvent from an organic layer. During the evaporation of the solvent, a very high temperature will thermally decompose DIBOC. Then, the evaporation is preferably carried out at a temperature not higher than 50° C. under reduced pressure.

As-produced DIBOC by the process of the present invention has already high purity and requires no purification by distillation in high vacuum which is usual in the conventional processes.

According to the present invention, DIBOC can be prepared using the alkali metal tert.-butoxide as one of the starting materials in one reaction vessel at a high yield and purity.

PREFERRED EMBODIMENTS OF THE INVENTION

The present invention will be illustrated by following Examples, which do not limit the scope of the present invention.

EXAMPLE 1

In a 5 liter four-necked flask equipped with a stirrer, a thermometer, a gas-inlet tube and a dropping funnel which had been replaced with nitrogen, potassium tert.-butoxide (336.6 g, 3 moles) and hexane (3.6 liters) were charged. Through a mixture in the flask, carbon dioxide gas (86.6 liters, 4 moles) was bubbled at 15° to 25° C. over 2 hours while stirring.

Then, the resulting slurry form mixture was cooled to 5° to 10° C., and to the mixture, methanesulfonyl chloride (171.8 g, 1.5 moles) was dropwise added at the same temperature, followed by stirring at 5° to 15° C. for three hours.

After the reaction, water (1 liter) was added to the reaction mixture, and the mixture was stirred for 30 minutes, kept standing and separated. The resulting organic layer was again washed with water (1 liter) and concentrated under reduced pressure at 35° to 40° C. to obtain colorless liquid di-tert.-butyl dicarbonate (285.8 g). Yield, 87%. This product was analyzed by gas chromatography to find that a purity was 99.7%. A melting point was 22°–23° C.

EXAMPLES 2-5

In the same manner as in Example 1 but changing a solvent and a temperature during the reaction with methanesulfonyl chloride as shown in Table 1, the reaction and post-treatment were carried out. A reaction time in the reaction with methanesulfonyl chloride, and a yield and a purity of obtained DIBOC are shown in Table 1.

TABLE 1

| Example No. | Solvent (volume ratio) | Reaction temp. (°C.) | Reaction time (hr) | Yield (%) | Purity (%) |
| --- | --- | --- | --- | --- | --- |
| 2 | Hexane | 20-30 | 1 | 75 | 99.9 |
| 3 | Hexane | −5-5 | 5 | 80 | 99.1 |
| 4 | Hexane/toluene (1/1) | 5-15 | 5 | 75 | 98.6 |
| 5 | Toluene | 5-15 | 5 | 72 | 99.0 |

EXAMPLE 6

In a 5 liter four-necked flask equipped with a stirrer, a thermometer, a gas-inlet tube and a dropping funnel which had been replaced with nitrogen, potassium tert.-butoxide (336.6 g, 3 moles) and hexane (3.6 liters) were charged. Through a mixture in the flask, carbon dioxide gas (86.6 liters, 4 moles) was bubbled at 15° to 25° C. over 2 hours while stirring.

Then, to the resulting slurry form mixture, N-laurylpyridinium chloride (42.6 g, 0.15 mole) was charged at room temperature and stirred at the same temperature for 30 minutes. After cooling to 5° to 10° C., methanesulfonyl chloride (171.8 g, 1.5·moles) was dropwise added at the same temperature, followed by stirring at 5° to 15° C. for 1.5 hours.

After the reaction, water (1 liter) was added to the reaction mixture, and the mixture was stirred for 30 minutes, kept standing and separated. The resulting organic layer was again washed with water (1 liter) and concentrated under reduced pressure at 35° to 40° C. to obtain colorless liquid di-tert.-butyl dicarbonate (291.4 g). Yield, 89%. This product was analyzed by gas chromatography to find that a purity was 98.9%.

EXAMPLE 7

In a 2 liter four-necked flask equipped with a stirrer, a thermometer, a gas-inlet tube and a dropping funnel which had been replaced with nitrogen, potassium tert.-butoxide (112.2 g, 1 mole) and hexane (1.2 liters) were charged. Through a mixture in the flask, carbon dioxide gas (26.9 liters, 1.2 moles) was bubbled at 0° to 10° C. over one hour while stirring.

Then, to the resulting slurry form mixture, pyridine (1.6 g, 0.02 mole) was charged at 0° to 10° C. and then methanesulfonyl chloride (57.3 g, 0.5 mole) was dropwise added at the same temperature, followed by stirring at the same temperature for 2.5 hours.

After the reaction, 5% sulfuric acid (250 ml) was added to the reaction mixture, and the mixture was stirred for 30 minutes, kept standing and separated. The resulting organic layer was washed with a 5% aqueous solution of sodium bicarbonate and water successively and concentrated under reduced pressure at 35° to 40° C. to obtain colorless liquid di-tert.-butyl dicarbonate (97.1 g). Yield, 89%. This product was analyzed by gas chromatography to find that a purity was 98.6%.

EXAMPLE 8

In a one liter four-necked flask equipped with a stirrer, a thermometer, a gas-inlet tube and a dropping funnel which had been replaced with nitrogen, potassium tert.-butoxide (112.1 g, 1 mole) and hexane (600 ml) were charged. Through a mixture in the flask, carbon dioxide gas (26.9 liters, 1.2 moles) was bubbled at −10° to 0° C. over one hour while stirring.

Then, to the resulting slurry form mixture, N-n-octylpyridinium chloride (11.4 g, 0.05 moles) and pyridine (11.4 g) were charged at 10° to −5° C. and then methanesulfonyl chloride (57.3 g, 0.5 mole) was dropwise added at the same temperature, followed by stirring at the same temperature for one hour.

After the reaction, 5% sulfuric acid (250 ml) was added to the reaction mixture, and the mixture was stirred for 30 minutes, kept standing and separated. The resulting organic layer was washed with a 5% aqueous solution of sodium bicarbonate and water successively and concentrated under reduced pressure at 35° to 40° C. to obtain colorless liquid di-tert.-butyl dicarbonate (98.2 g). Yield, 90%. This product was analyzed by gas chromatography to find that a purity was 99.3%.

EXAMPLE 9

In a 5 liter four-necked flask equipped with a stirrer, a thermometer, a gas-inlet tube and a dropping funnel which had been replaced with nitrogen, sodium tert.-butoxide (288.3 g, 3 moles) and hexane (3.6 liters) were charged. Through a mixture in the flask, carbon dioxide gas (86.6 liters, 4 moles) was bubbled at 15° to 25° C. over 2 hours while stirring.

Then, to the resulting slurry form mixture, N-laurylpyridinium chloride (42.6 g, 0.15 moles) was charged at room temperature and stirred at the same temperature for 30 minutes. After cooling to 5° to 10° C., methanesulfonyl chloride (171.8 g, 1.5 moles) was dropwise added at the same temperature, followed by stirring at 5° to 15° C. for 3 hours.

After the reaction, water (1 liter) was added to the reaction mixture, and the mixture was stirred for 30 minutes, kept standing and separated. The resulting organic layer was again washed with water (1 liter) and concentrated under reduced pressure at 35° to 40° C. to obtain colorless liquid di-tert.-butyl dicarbonate (261.9 g). Yield, 80%. This product was analyzed by gas chromatography to find that a purity was 99.3%. A melting point was 22°-23° C.

EXAMPLES 10-16

In the same manner as in Example 9 but using a solvent of Table 2 in place of hexaene and a phase transfer catalyst of Table 2 in place of N-laurylpyridinium chloride, the reaction and post-treatment were carried out. A yield and a purity of obtained DIBOC are shown in Table 2.

TABLE 2

| Example No. | Solvent | Phase transfer catalyst | Yield (%) | Purity (%) |
| --- | --- | --- | --- | --- |
| 10 | Toluene | Lauryltrimethylammonium chloride | 75 | 99.5 |
| 11 | Toluene | Benzyltrimethylammonium chloride | 72 | 99.7 |
| 12 | Toluene | N-Laurylpyridinium chloride | 78 | 99.6 |
| 13 | Toluene | Methyltri-n-octylammonium | 77 | 95.6 |

TABLE 2-continued

| Example No. | Solvent | Phase transfer catalyst | Yield (%) | Purity (%) |
|---|---|---|---|---|
| | | chloride | | |
| 14 | Heptane | N-Laurylpyridinium chloride | 76 | 99.7 |
| 15 | Hexane | N-Lauryl-4-picolinium chloride | 82 | 99.3 |
| 16 | Hexane | N-Benzylpyridinium chloride | 77 | 99.1 |

EXAMPLES 17 AND 18

In the same manner as in Example 9 but changing a temperature during the reaction with methanesulfonyl chloride as shown in Table 3, the reaction and post-treatment were carried out. A reaction time with methanesulfonyl chloride, and a yield and a purity of obtained DIBOC are shown in Table 3.

TABLE 3

| Example No. | Reaction temp. (°C.) | Reaction time (hr) | Yield (%) | Purity (%) |
|---|---|---|---|---|
| 17 | 20–30 | 2 | 72 | 99.5 |
| 18 | −5–5 | 7 | 82 | 99.1 |

EXAMPLE 19

In a 2 liter four-necked flask equipped with a stirrer, a thermometer, a gas-inlet tube and a dropping funnel which had been replaced with nitrogen, sodium tert.-butoxide (96.1 g, 1 mole) and hexane (1.2 liters) were charged. Through a mixture in the flask, carbon dioxide gas (26.9 liters, 1.2 moles) was bubbled at 0° to 10° C. over one hour while stirring.

Then, to the resulting slurry form mixture, pyridine (1.6 g, 0.02 moles) was charged at 0° to 10° C. and then methanesulfonyl chloride (57.3 g, 0.5 mole) was dropwise added to the same temperature, followed by stirring at the same temperature for 3 hours.

After the reaction, 5% sulfuric acid (250 ml) was added to the reaction mixture, and the mixture was stirred for 30 minutes, kept standing and separated. The resulting organic layer was washed with a 5% aqueous solution of sodium bicarbonate and water successively and concentrated under reduced pressure at 35° to 40° C. to obtain colorless liquid di-tert.-butyl dicarbonate (77.5 g). Yield, 71%. This product was analyzed by high performance liquid chromatography to find that a purity was 99.1%.

EXAMPLE 20

In a one liter four-necked flask equipped with a stirrer, a thermometer, a gas-inlet tube and a dropping funnel which had been replaced with nitrogen, sodium tert.-butoxide (96.1 g, 1 mole) and hexane (600 ml) were charged. Through a mixture in the flask, carbon dioxide gas (26.9 liters, 1.2 moles) was bubbled at −10° to 0° C. over one hour while stirring.

Then, to the resulting slurry form mixture, N-n-octyl-pyridinium chloride (11.4 g, 0.05 mole) was charged at −10° to −5° C. and then methanesulfonyl chloride (57.3 g, 0.5 mole) was dropwise added at the same temperature, followed by stirring at the same temperature for 3 hours.

After the reaction, 5% sulfuric acid (250 ml) was added to the reaction mixture, and the mixture was stirred for 30 minutes, kept standing and separated. The resulting organic layer was washed with a 5% aqueous solution of sodium bicarbonate and water successively and concentrated under reduced pressure at 35° to 40° C. to obtain colorless liquid di-tert.-butyl dicarbonate (90.6 g). Yield, 83%. This product was analyzed by gas chromatography to find that a purity was 99.4%.

EXAMPLES 21–24

In the same manner as in Example 20 but using a phase transfer catalyst of Table 4 in place of N-n-octylpyridinium chloride and an aromatic amine of Table 4 in place of pyridine, the reaction and post-treatment were carried out. A yield and a purity of obtained DIBOC are shown in Table 4.

TABLE 4

| Example No. | Phase transfer catalyst (g) | Aromatic amine (g) | Yield (%) | Purity (%) |
|---|---|---|---|---|
| 21 | N-n-Octyl-4-picolinium chloride (12.1) | 4-Picoline (12.1) | 71 | 99.5 |
| 22 | N-n-Octyl-pyridinium bromide (13.6) | Pyridine (13.6) | 74 | 97.5 |
| 23 | N-Lauryl-pyridinium bromide (16.4) | Pyridine (16.4) | 80 | 97.7 |
| 24 | N-n-Octyl-pyridinium chloride (2.3) | Pyridine (2.3) | 80 | 99.3 |

EXAMPLES 25 AND 26

In the same manner as in Example 20 but changing a temperature during the reaction with methanesulfonyl chloride as shown in Table 5, the reaction and post-treatment were carried out. A reaction time in the reaction with methanesulfonyl chloride, and a yield and a purity of obtained DIBOC are shown in Table 5.

TABLE 5

| Example No. | Reaction temp. (°C.) | Reaction time (hr) | Yield (%) | Purity (%) |
|---|---|---|---|---|
| 25 | 0–10 | 2 | 76 | 99.2 |
| 26 | −35–−25 | 10 | 72 | 98.9 |

COMPARATIVE EXAMPLE 1

In the same manner as in Example 1 but changing a temperature during the reaction with methanesulfonyl chloride to 60°–70° C., the reaction and post-treatment were carried out. During the reaction with methanesulfonyl chloride, gas was vigorously generated. Yield of DIBOC, 11%. Purity of DIBOC, 93.2%.

COMPARATIVE EXAMPLE 2

In a 300 ml four-necked flask equipped with a stirrer, a thermometer, a gas-inlet tube and a dropping funnel which had been replaced with nitrogen, potassium tert.-butoxide (11.2 g, 0.1 mole) and toluene (180 ml) were charged. Through a mixture in the flask, carbon dioxide gas (2.9 liters, 0.13 mole) was bubbled at 15° to 15° C. over 30 minutes while stirring.

Then, to the resulting slurry form mixture, N,N-dimethylformamide (15 ml) was charged. After cooling to 5° to 10° C., methanesulfonyl chloride (5.7 g, 0.05 mole) was dropwise added at the same temperature, followed by stirring at 5° to 15° C. for 20 hours.

After the reaction, water (50 ml) was added to the reaction mixture, and the mixture was stirred for 30 minutes, kept standing and separated. The resulting organic layer was again washed with water (50 ml) and concentrated under reduced pressure at 35° to 40° C. to obtain pale yellow liquid di-tert.-butyl dicarbonate (2.6 g). Yield, 24%. Purity, 98.8%.

COMPARATIVE EXAMPLE 3

In the same manner as in Comparative Example 2 but using tert.-butyl alcohol in place of N,N-dimethylformamide, the reaction and post-treatment were carried out to obtain colorless liquid di-tert.-butyl dicarbonate (2.3 g). Yield 21%. Purity, 99.0%.

COMPARATIVE EXAMPLE 4

In the same manner as in Example 9 but changing a temperature during the reaction with methanesulfonyl chloride to 60°-70° C., the reaction and post-treatment were carried out. During the reaction with methanesulfonyl chloride, gas was vigorously generated. Yield of DIBOC, 5%. Purity, 81.5%.

COMPARATIVE EXAMPLE 5

In a 2 liter four-necked flask equipped with a stirrer, a thermometer, a gas-inlet tube and a dropping funnel which had been replaced with nitrogen, sodium tert.-butoxide (96.1 g, 1 mole) and toluene (1.2 liters) were charged. Through a mixture in the flask, carbon dioxide gas (26.9 liters, 1.2 moles) were bubbled at 0° to 10° C. over one hour while stirring.

Then, to the resulting slurry form mixture, pyridine (100 ml) and benzyltriethylammonium chloride (2.3 g, 10 millimoles) were charged at room temperature. Then, a mixture of p-toluenesulfonyl chloride (76.3 g, 0.4 mole) and toluene (30 ml) was charged, followed by heating to 50° C. and stirring at the same temperature for 1.5 hours.

After the reaction, the reaction mixture was cooled to 5° to 10° C., and 5% sulfuric acid (250 ml) was added to the reaction mixture. The mixture was stirred for 30 minutes, kept standing and separated. The resulting organic layer was washed with a 5% aqueous solution of sodium bicarbonate and water successively and concentrated under reduced pressure at 35° to 40° C. to obtain a dark brown liquid (75.4 g). This product was analyzed by gas chromatography to find that it contained 92.7% by DIBOC and 5.75% of unreacted p-toluenesulfonyl chloride.

The dark brown liquid was then purified by distillation under reduced pressure to obtain colorless liquid DIBOC (62.9 g). Boiling point, 56°-58° C./0.5 mmHg. Yield, 57.6% (based on the amount of sodium tert.-butoxide). A purity of this product was analyzed by gas chromatography and found to be 99.0%. A recovery ratio of DIBOC by distillation was 89%.

COMPARATIVE EXAMPLE 6

In the same manner as in Comparative Example 5 but using 95.3 g (0.5 mole) of p-toluenesulfonyl chloride, the reaction was carried out, but it took eleven (11) hours before p-toluenesulfonyl chloride disappeared.

After the reaction, the reaction mixture was post-treated in the same manner as in Comparative Example 5 to obtain a dark brown liquid (47.8 g). This liquid was analyzed by gas chromatography to find that it contained 94.9% of DIBOC.

By monitoring the reaction by gas chromatography, it was confirmed that DIBOC was decomposed during the reaction.

What is claimed is:

1. A process for preparing di-tert.-butyl dicarbonate which comprises reacting alkali metal tert.-butyl carbonate with methanesulfonyl chloride.

2. The process according to claim 1, wherein said alkali metal tert.-butyl carbonate is sodium tert.-butyl carbonate or potassium tert.-butyl carbonate.

3. The process according to claim 1, wherein sodium tert.-butyl carbonate is reacted with methanesulfonyl chloride in the presence of at least one catalyst selected from a phase transfer catalyst and an aromatic amine.

4. The process according to claim 3, wherein said phase transfer catalyst is at least one selected from the group consisting of quaternary ammonium salts and pyridinium salts.

5. The process according to claim 3, wherein said phase transfer catalyst is an N-alkylpyridinium salt.

6. The process according to claim 3, wherein said aromatic amine is pyridine.

7. The process according to claim 1, wherein potassium tert.-butyl carbonate is reacted with methanesulfonyl chloride in the presence of at least one catalyst selected from phase transfer catalysts and aromatic amines.

8. The process according to claim 7, wherein said phase transfer catalyst is at least one selected from the group consisting of a quaternary ammonium salt and a pyridinium salt.

9. The process according to claim 7, wherein said phase transfer catalyst is an N-alkylpyridinium salt.

10. The process according to claim 7, wherein said aromatic amine is pyridine.

11. The process according to claim 1, wherein the reaction is carried out in a solvent selected from the group consisting of aliphatic hydrocarbons and aromatic hydrocarbons.

12. The process according to claim 1, wherein a reaction temperature is from −50° C. to +50° C.

* * * * *